US012773113B2

(12) United States Patent
Messerly

(10) Patent No.: US 12,773,113 B2
(45) Date of Patent: Oct. 27, 2026

(54) PHOTOACOUSTIC MEDICAL-DEVICE NAVIGATION SYSTEM AND METHODS

(71) Applicant: Bard Access Systems, Inc., Salt Lake City, UT (US)

(72) Inventor: Shayne Messerly, Kaysville, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

(21) Appl. No.: 18/809,024

(22) Filed: Aug. 19, 2024

(65) Prior Publication Data

US 2026/0047763 A1 Feb. 19, 2026

(51) Int. Cl.

*A61B 5/00* (2006.01)
*A61B 34/20* (2016.01)
*A61M 25/01* (2006.01)

(52) U.S. Cl.

CPC .......... *A61B 5/0095* (2013.01); *A61B 5/6852* (2013.01); *A61B 5/742* (2013.01);
(Continued)

(58) Field of Classification Search

CPC ....... A61B 5/0095; A61B 5/061; A61B 34/20; A61B 5/6852; A61B 5/742
See application file for complete search history.

(56) References Cited

U.S. PATENT DOCUMENTS 8,388,541 B2 3/2013 Messerly et al.
8,781,555 B2 7/2014 Burnside et al.
(Continued)

FOREIGN PATENT DOCUMENTS

WO 2020242887 A1 12/2020
WO 2021255013 A1 12/2021
WO 2025198858 A1 9/2025

OTHER PUBLICATIONS

Li, M., Tang, Y. and Yao, J., 2018. Photoacoustic tomography of blood oxygenation: a mini review. Photoacoustics, 10, pp. 65-73.
(Continued)

*Primary Examiner* — John D Li
(74) *Attorney, Agent, or Firm* — Rutan & Tucker LLP

(57) ABSTRACT

Photoacoustic medical-device navigation systems and methods provide alternatives to those incorporating fluoroscopy for medical-device navigation in patient bodies. A medical-device navigation system can include an optical-fiber stylet, ultrasound transducers, and a console. The stylet can transmit light to an instant location of a distal tip of an elongate medical device in a patient's body and, thereby, irradiate endogenous chromophores to generate ultrasound-frequency photoacoustic pressure waves therefrom. The ultrasound transducers can detect ultrasound signals corresponding to the photoacoustic pressure waves. The console can instantiate medical-device navigation processes for navigating the elongate medical device via the stylet as the elongate medical device is advanced to the target location in the patient's body. The medical-device navigation processes can include acquiring ultrasound-signal data from the ultrasound transducers, reconstructing images from the ultrasound-signal data, and displaying reconstructed images on a display for navigating the elongate medical device to the target location in the patient's body.

23 Claims, 13 Drawing Sheets

(52) U.S. Cl.
CPC .......... *A61B 34/20* (2016.02); *A61B 2576/00* (2013.01); *A61M 25/0102* (2013.01); *A61M 2025/0166* (2013.01)

(56) References Cited

U.S. PATENT DOCUMENTS

| | | | | |
|---|---|---|---|---|
| 8,849,382 | B2 | 9/2014 | Cox et al. | |
| 9,636,031 | B2 | 5/2017 | Cox | |
| 9,649,048 | B2 | 5/2017 | Cox et al. | |
| 2007/0093717 | A1 * | 4/2007 | Nagar .................... | A61B 5/489 600/438 |
| 2014/0058253 | A1 | 2/2014 | Prough et al. | |
| 2014/0378796 | A1 * | 12/2014 | Chen .................... | A61B 5/7207 600/328 |
| 2015/0208925 | A1 | 7/2015 | Bagwell et al. | |
| 2018/0310831 | A1 | 11/2018 | Cheng et al. | |
| 2019/0380679 | A1 | 12/2019 | Bharat et al. | |

OTHER PUBLICATIONS

Xia, J., Yao, J. and Wang, L.V., 2014. Photoacoustic tomography: principles and advances. Electromagnetic waves (Cambridge, Mass.), 147, p. 1.).

Zhou, Y., Yao, J. and Wang, L.V., 2016. Tutorial on photoacoustic tomography. Journal of biomedical optics, 21(6), pp. 061007-061007.

PCT/US2025/042271 filed Aug. 15, 2025 International Search Report and Written Opinion dated Oct. 24, 2025.

Xia Wenfeng et al: "Interventional multispectral photoacoustic imaging with a clinical linear array ultrasound probe for guiding nerve blocks", Progress in Biomedical Optics and Imaging, SPIE—Engineering, Bellingham, WA, US, vol. 9708, Mar. 15, 2016 (Mar. 15, 2016), pp. 97080C-97080C, XP060064562, ISSN: 1605-7422, DOI: 10.1117/12.2209047, ISBN: 978-1-5106-0027-0, pp. 2-4.

* cited by examiner

PHOTOACOUSTIC MEDICAL-DEVICE NAVIGATION SYSTEM AND METHODS

BACKGROUND

Navigation and appropriate placement of medical devices including needles, catheters, and the like are important for patient (and clinician) safety and clinical outcomes. Ultrasound methods are typically used for navigation of needles into patient vasculatures and determination of whether distal tips of the needles are appropriately placed in their target vascular locations. However, such ultrasound methods are highly dependent upon vascular visibility in ultrasound images, needle visibility in the ultrasound images, and operator experience. Fluoroscopic methods are typically used for navigation of catheters through patient vasculatures and determination of whether distal tips of the catheters are appropriately placed in their target vascular locations. However, such fluoroscopic methods expose patients and, possibly, their clinicians to harmful X-ray radiation. Moreover, the patients can be exposed to potentially harmful contrast media needed for the fluoroscopic methods. As such, alternative navigation means for navigating medical devices are needed.

Disclosed herein are photoacoustic medical-device navigation systems and methods that address at least the foregoing.

SUMMARY

Disclosed herein is a medical-device navigation system for navigating an elongate medical device to a target location in a body of a patient. The medical-device navigation system includes, in some embodiments, a stylet, a plurality of ultrasound transducers, and a console. The stylet includes an optical fiber along a length of the stylet. The optical fiber is configured to transmit light to an instant location of a distal tip of the elongate medical device in the body of the patient and, thereby, irradiate one or more endogenous chromophores in the instant location to generate ultrasound-frequency photoacoustic pressure waves therefrom. The ultrasound transducers are configured to detect ultrasound signals propagated through one or more tissues of the patient corresponding to the photoacoustic pressure waves generated from the one or more endogenous chromophores. The console includes electronic components and circuitry including memory and one or more processors. The memory includes executable instructions configured to instantiate medical-device navigation processes upon execution by the processor(s) for navigating the elongate medical device by way of the stylet disposed therein as the elongate medical device is advanced to the target location in the body of the patient. The medical-device navigation processes include a data-acquisition process that utilizes data-acquisition logic for acquiring ultrasound-signal data from the ultrasound transducers and writing the ultrasound-signal data to the memory of the console. The medical-device navigation processes also include an image-reconstruction process that utilizes image-reconstruction logic for reconstructing images from the ultrasound-signal data and writing image data to the memory of the console. The medical-device navigation processes also include a displaying process that utilizes displaying logic for displaying reconstructed images from the image data on a display for navigating the elongate medical device to the target location in the body of the patient.

In some embodiments, the medical-device navigation processes also include an irradiation process that utilizes irradiation logic for irradiating the one or more endogenous chromophores in the instant location with the light transmitted by the optical fiber. The light transmitted by the optical fiber is a pulsed light or intensity-modulated continuous light for optical absorption and thermoelastic expansion of the one or more endogenous chromophores.

In some embodiments, the optical absorption and thermoelastic expansion of the one or more endogenous chromophores and, thus, the photoacoustic pressure waves and the corresponding ultrasound signals vary in accordance with the pulsed light or the intensity-modulated continuous light.

In some embodiments, the medical-device navigation processes also include a signal-processing process that utilizes signal-processing logic for at least extracting time-of-flight information from the ultrasound-signal data.

In some embodiments, the medical-device navigation processes also include a mapping process that utilizes mapping logic for mapping the ultrasound signals from different ultrasound transducers to common photoacoustic pressure-wave sources or events with the time-of-flight information and speed of sound in the instant location of the distal tip of the elongate medical device in the body of the patient.

In some embodiments, the image-reconstruction process reconstructs the images for navigating the elongate medical device by projecting mapped ultrasound signals from the mapping process back along their possible paths from the different ultrasound transducers to the common photoacoustic pressure-wave sources or events.

In some embodiments, the one or more endogenous chromophores are selected from at least oxygenated hemoglobin, reduced hemoglobin, oxygenated myoglobin, reduced myoglobin, melanin, and one or more lipids.

In some embodiments, the ultrasound transducers are disposed in a sensor array of an ultrasound probe.

In some embodiments, the ultrasound transducers are disposed in a plurality of patient-wearable patches.

In some embodiments, the stylet is configured to removably insert into a lumen of the elongate medical device.

In some embodiments, the stylet is integrated into the elongate medical device.

Also disclosed herein is a method of a medical-device navigation system for navigating an elongate medical device to a target location in a body of a patient. The method includes, in some embodiments, instantiating medical-device navigation processes upon executing executable instructions stored in memory of a console by one or more processors of the console. The medical-device navigation processes are for navigating the elongate medical device by way of an optical-fiber stylet disposed therein as the elongate medical device is advanced to the target location in the body of the patient. The method also includes transmitting light along a length of the stylet to an instant location of a distal tip of the elongate medical device in the body of the patient and, thereby, irradiating one or more endogenous chromophores in the instant location to generate ultrasound-frequency photoacoustic pressure waves therefrom. The method also includes detecting ultrasound signals with a plurality of ultrasound transducers, wherein the ultrasound signals are propagated through one or more tissues of the patient corresponding to the photoacoustic pressure waves generated from the one or more endogenous chromophores. The method also includes acquiring ultrasound-signal data from the ultrasound transducers and writing the ultrasound-signal data to the memory of the console in accordance with a data-acquisition process that utilizes data-acquisition logic. The method also includes reconstructing images from the ultrasound-signal data and writing image data to the memory of the console in accordance with an image-reconstruction process that utilizes image-reconstruction logic. The method also includes displaying reconstructed images from the image data on a display in accordance with a displaying process that utilizes displaying logic for navigating the elongate medical device to the target location in the body of the patient.

In some embodiments, the method further includes irradiating the one or more endogenous chromophores in the instant location with the light transmitted by the optical fiber. The light transmitted by the optical fiber is a pulsed light or intensity-modulated continuous light in accordance with an irradiation process that utilizes irradiation logic for optical absorption and thermoelastic expansion of the one or more endogenous chromophores.

In some embodiments, the thermoelastic expansion of the one or more endogenous chromophores and, thus, the photoacoustic pressure waves and the corresponding ultrasound signals vary in accordance with the pulsed light or the intensity-modulated continuous light.

In some embodiments, the metho further includes extracting time-of-flight information from the ultrasound-signal data in accordance with a signal-processing process that utilizes signal-processing logic.

In some embodiments, the method further includes mapping the ultrasound signals from different ultrasound transducers to common photoacoustic pressure-wave sources or events with the time-of-flight information and speed of sound in the instant location of the distal tip of the elongate medical device in the body of the patient in accordance with a mapping process that utilizes mapping logic.

In some embodiments, the image-reconstruction process reconstructs the images for navigating the elongate medical device by projecting mapped ultrasound signals from the mapping process back along their possible paths from the different ultrasound transducers to the common photoacoustic pressure-wave sources or events.

In some embodiments, the one or more endogenous chromophores are selected from at least oxygenated hemoglobin, reduced hemoglobin, oxygenated myoglobin, reduced myoglobin, melanin, and one or more lipids.

In some embodiments, the ultrasound transducers are disposed in a sensor array of an ultrasound probe.

In some embodiments, the ultrasound transducers are disposed in a plurality of patient-wearable patches.

In some embodiments, the stylet is configured to removably insert into a lumen of the elongate medical device.

In some embodiments, the stylet is integrated into the elongate medical device.

Also disclosed herein is a medical-device navigation system for navigating an elongate medical device to a target location in a body of a patient. The medical-device navigation system includes, in some embodiments, a stylet, a plurality of ultrasound transducers embodied in a plurality of patient-wearable patches, and a console. The stylet includes an optical fiber along a length of the stylet. The optical fiber is configured to transmit light to an instant location of a distal tip of the elongate medical device in the body of the patient and, thereby, irradiate one or more endogenous chromophores in the instant location to generate ultrasound-frequency photoacoustic pressure waves therefrom. The ultrasound transducers are configured to detect ultrasound signals propagated through one or more tissues of the patient corresponding to the photoacoustic pressure waves generated from the one or more endogenous chromophores.

The console includes electronic components and circuitry including memory and one or more processors. The memory includes executable instructions configured to instantiate medical-device navigation processes upon execution by the processor(s) for navigating the elongate medical device by way of the stylet disposed therein as the elongate medical device is advanced to the target location in the body of the patient. The medical-device navigation processes include a data-acquisition process that utilizes data-acquisition logic for acquiring ultrasound-signal data from the ultrasound transducers and writing the ultrasound-signal data to the memory of the console. The medical-device navigation processes also include a tracking process that utilizes tracking logic for generating a tracking path from the ultrasound-signal data and writing tracking data to the memory of the console. The medical-device navigation processes also include a displaying process that utilizes displaying logic for displaying the tracking path from the tracking data on a display for navigating the elongate medical device to the target location in the body of the patient.

These and other features of the concepts provided herein will become more apparent to those of skill in the art in view of the accompanying drawings and following description, which describe particular embodiments of such concepts in greater detail.

DESCRIPTION

Figure 1:
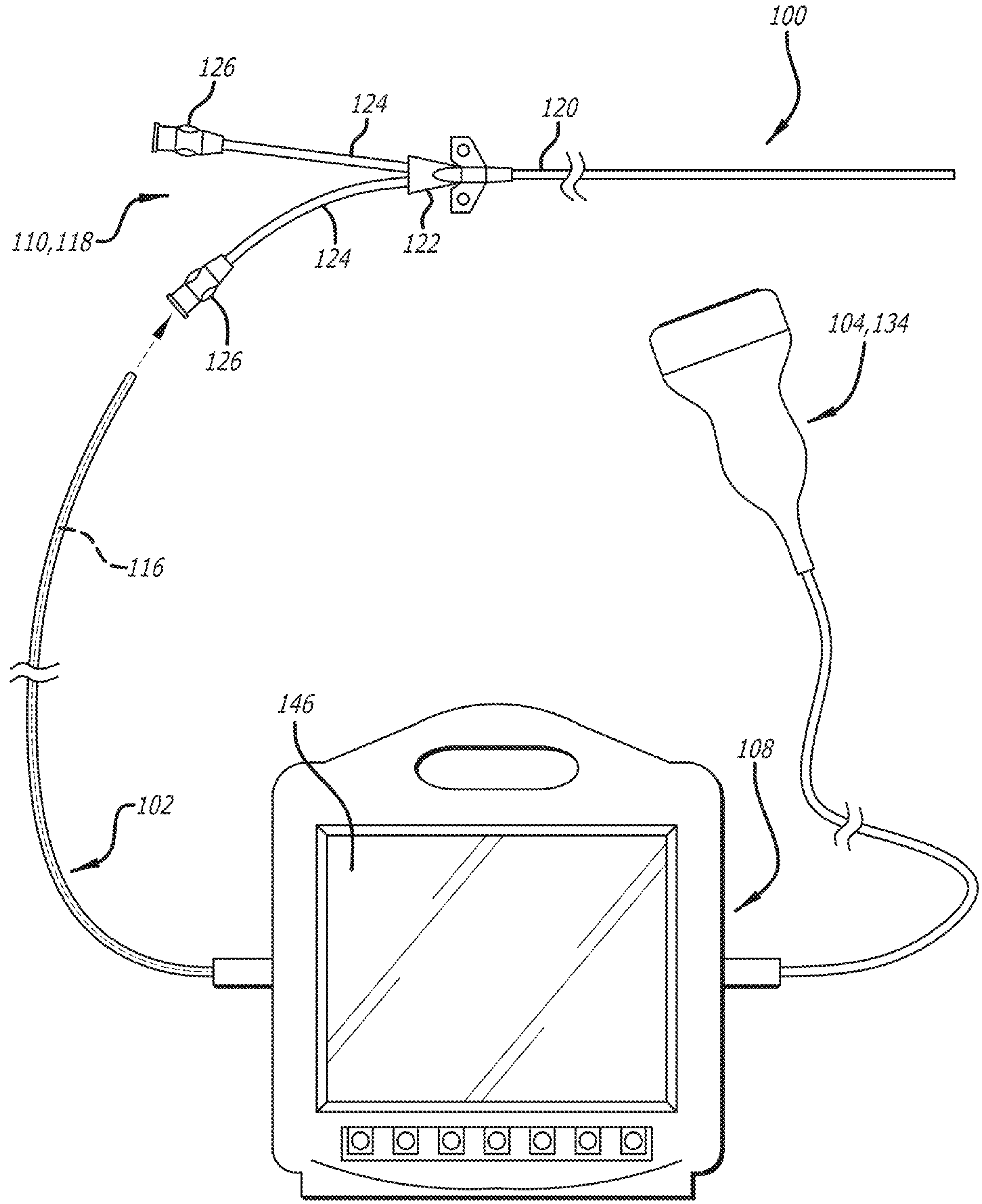
FIG. 1 illustrates a medical-device navigation system in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. In addition, any of the foregoing features or steps can, in turn, further include one or more features or steps unless indicated otherwise. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

"Proximal" is used to indicate a portion, section, piece, element, or the like of a medical device intended to be near or relatively nearer to a clinician when the medical device is used on a patient. For example, a "proximal portion" or "proximal section" of the medical device includes a portion or section of the medical device intended to be near the clinician when the medical device is used on the patient. Likewise, a "proximal length" of the medical device includes a length of the medical device intended to be near the clinician when the medical device is used on the patient. A "proximal end" of the medical device is an end of the medical device intended to be near the clinician when the medical device is used on the patient. The proximal portion, the proximal section, or the proximal length of the medical device need not include the proximal end of the medical device. Indeed, the proximal portion, the proximal section, or the proximal length of the medical device can be short of the proximal end of the medical device. However, the proximal portion, the proximal section, or the proximal length of the medical device can include the proximal end of the medical device. Should context not suggest the proximal portion, the proximal section, or the proximal length of the medical device includes the proximal end of the medical device, or if it is deemed expedient in the following description, "proximal portion," "proximal section," or "proximal length" can be modified to indicate such a portion, section, or length includes an end portion, an end section, or an end length of the medical device for a "proximal end portion," a "proximal end section," or a "proximal end length" of the medical device, respectively.

"Distal" is used to indicate a portion, section, piece, element, or the like of a medical device intended to be near, relatively nearer, or even in a patient when the medical device is used on the patient. For example, a "distal portion" or "distal section" of the medical device includes a portion or section of the medical device intended to be near, relatively nearer, or even in the patient when the medical device is used on the patient. Likewise, a "distal length" of the medical device includes a length of the medical device intended to be near, relatively nearer, or even in the patient when the medical device is used on the patient. A "distal end" of the medical device is an end of the medical device intended to be near, relatively nearer, or even in the patient when the medical device is used on the patient. The distal portion, the distal section, or the distal length of the medical device need not include the distal end of the medical device. Indeed, the distal portion, the distal section, or the distal length of the medical device can be short of the distal end of the medical device. However, the distal portion, the distal section, or the distal length of the medical device can include the distal end of the medical device. Should context not suggest the distal portion, the distal section, or the distal length of the medical device includes the distal end of the medical device, or if it is deemed expedient in the following description, "distal portion," "distal section," or "distal length" can be modified to indicate such a portion, section, or length includes an end portion, an end section, or an end length of the medical device for a "distal end portion," a "distal end section," or a "distal end length" of the medical device, respectively.

"Navigation" of an elongate medical device by way of any photoacoustic medical-device navigation system or method disclosed herein encompasses tracking of the elongate medical device, guidance of the elongate medical device, or both tracking and guidance of the elongate medical device with the photoacoustic medical-device navigation system or method, as the case might be. Notably, with a clinician's (or computer's) understanding of patient vasculature, imaging can be correlated with expected patient vasculature, as needed, for medical-device tracking.

"Location" is used to indicate a location of an elongate medical device, the stylet disposed therein, or the optical fiber thereof in some spatial or coordinate reference system such as a patient-based reference frame disclosed herein. Reference points for locating the elongate medical device in the patient-based reference frame can be provided by at least the patient-wearable patches.

Figure 7:
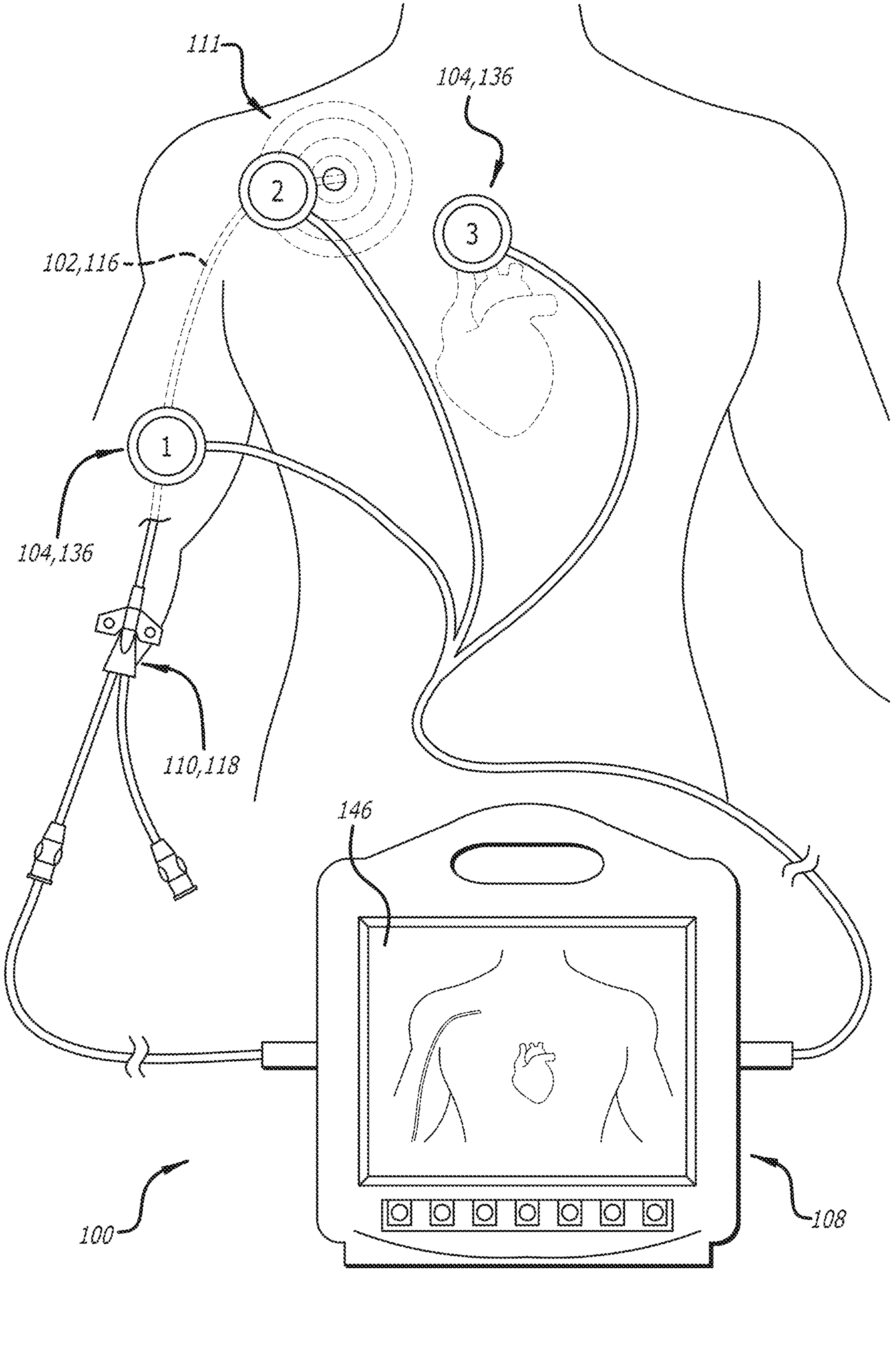
FIG. 7 illustrates navigation of the catheter in the body of the patient with the medical-device navigation system and a plurality of patient-wearable ultrasound-transducer patches thereof in accordance with some embodiments.

"Orientation" is used to indicate an orientation of an elongate medical device, the stylet disposed therein, or the optical fiber thereof in its location. By way of example, a distal tip of the elongate medical device graphically represented within the patient-based reference frame in FIG. 7 is in the superior vena cava with an orientation toward the right atrium of the heart.

"Logic" can be hardware, firmware, or software configured to perform one or more functions. As hardware, logic can include circuitry having data processing functionality, data storage functionality, or both. An example of such circuitry can include, but is not limited to, a hardware processor (e.g., a microprocessor, one or more processor cores, a digital-signal processor ["DSP"], a programmable gate array ["PGA"], a microcontroller, an application-specific integrated circuit ["ASIC"], etc.) or semiconductor memory. As firmware, the logic can be stored in persistent storage. As software, logic can include one or more processes, instances, Application Programming Interfaces ("APIs"), subroutines, functions, applets, servlets, or routines. Logic can also include source code, object code, a shared library, a dynamic link library ("DLL"), or even one or more instructions. Such software can be stored in any type of suitable non-transitory computer-readable storage medium or transitory storage medium (e.g., electrical, optical, acoustical, or any other form of propagated signal including carrier waves, infrared signals, or digital signals). An example of a non-transitory computer-readable storage medium can include, but is not limited to, a programmable circuit; non-persistent storage such as volatile memory (e.g., any type of random-access memory ["RAM"]); or persistent storage such as non-volatile memory (e.g., read-only memory ["ROM"], power-backed RAM, flash memory, phase-change memory, etc.), a solid-state drive, a hard-disk drive, an optical-disc drive, or a portable memory device.

Unless defined otherwise, all technical and scientific terms used herein have the same meaning as commonly understood by those of ordinary skill in the art.

As set forth above, navigation and appropriate placement of medical devices including needles, catheters, and the like are important for patient (and clinician) safety and clinical outcomes. Recognizing the need for alternative navigation means to ultrasound and fluoroscopy for navigating various medical devices to their target vascular locations, disclosed herein are photoacoustic medical-device navigation systems and methods for navigation and appropriate placement of medical devices.

Figure 2:
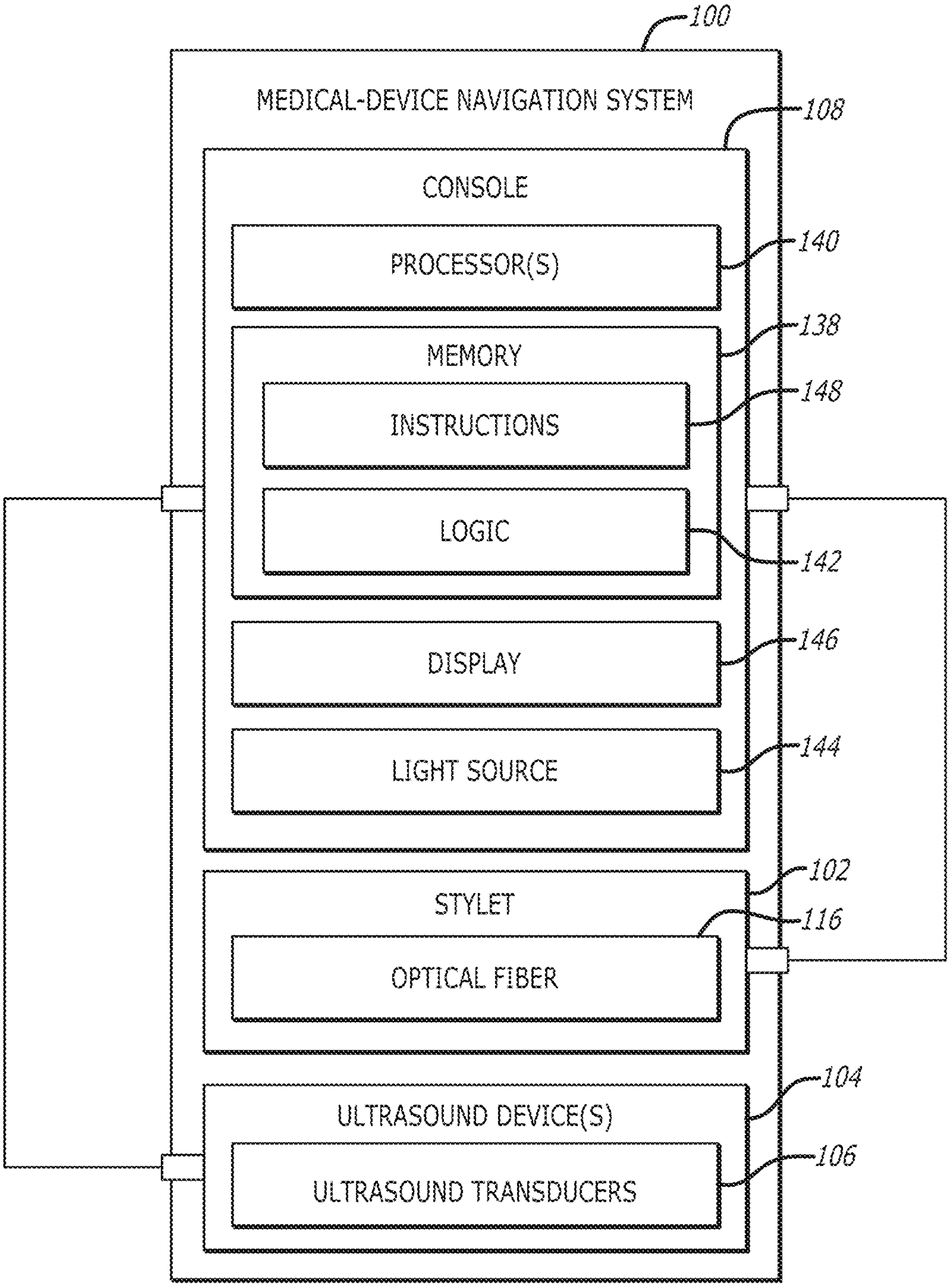
FIG. 2 illustrates a block diagram of the medical-device navigation system in accordance with some embodiments.

FIGS. 1 and 2 illustrate a medical-device navigation system 100 in accordance with some embodiments.

As shown, the medical-device navigation system 100 can include a stylet 102, one or more ultrasound devices 104 including a plurality of ultrasound transducers 106, and a console 108. Such a medical-device navigation system 100 is thereby configured for navigating an elongate medical device 110 to a target location in a body of a patient, particularly, by way of the stylet 102 disposed in the elongate medical device 110, as the elongate medical device 110 is advanced to the target location in the body of the patient. Notably, the medical-device navigation system 100 utilizes the photoacoustic effect to generate ultrasound signals 111 at an instant location of a distal tip of the elongate medical device 110 in the body of the patient, which ultrasound signals 111 can be detected and acquired for imaging successive locations in the body of the patient, tracking the distal tip of the elongate medical device 110 across the successive locations in the body of the patient, or both for up to at least two navigation modalities.

Figure 12:
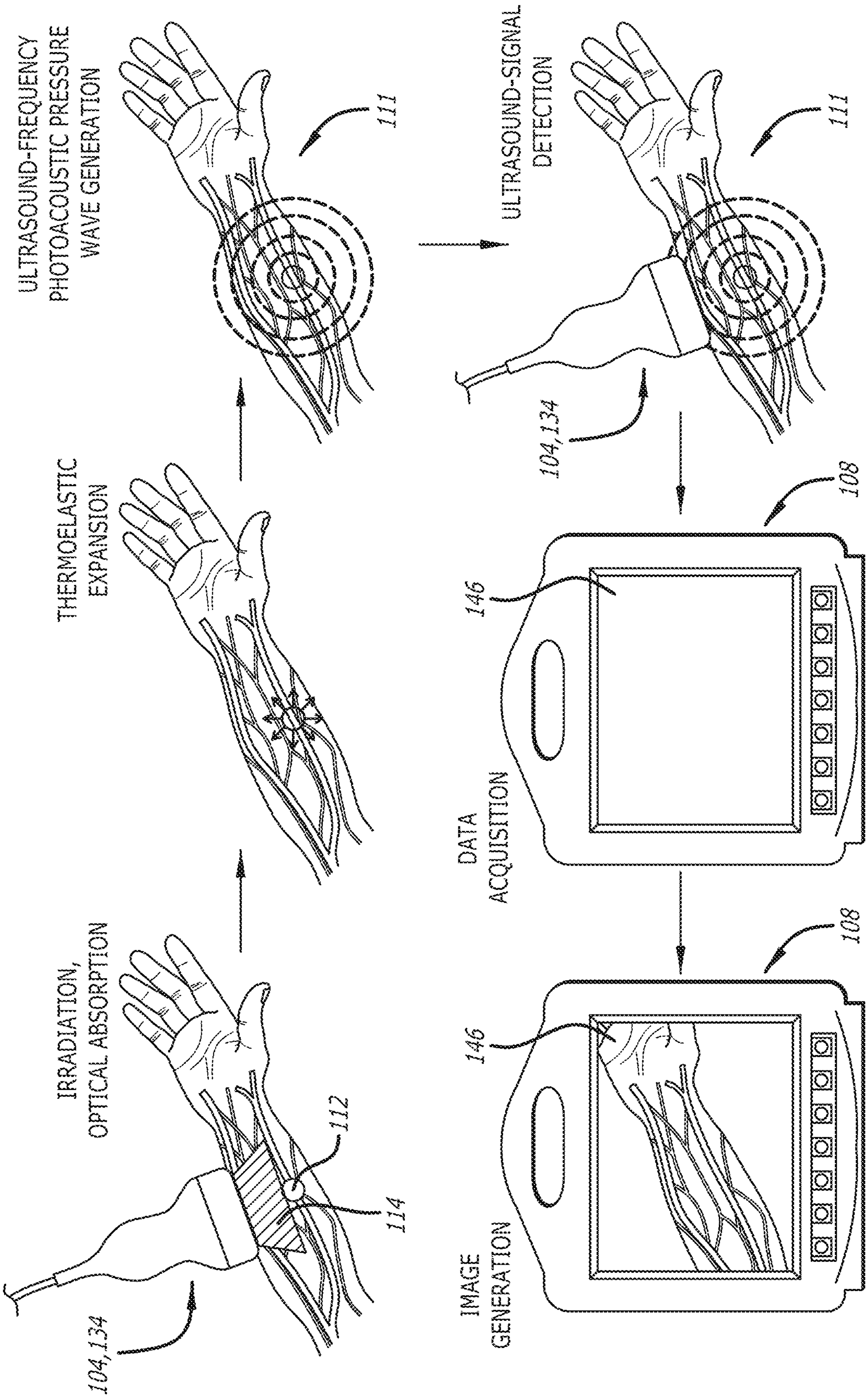
FIG. 12 illustrates a mechanistic overview of the medical-device navigation system using the ultrasound probe to both irradiate the one or more endogenous chromophores and detect the ultrasound signals corresponding to the photoacoustic pressure waves generated therefrom in accordance with some embodiments.

FIG. 12 illustrates a mechanistic overview of the photoacoustic effect utilized by the medical-device navigation system 100 in accordance with some embodiments.

As shown, irradiation of one or more endogenous chromophores 112 in a body of a patient with light 114 generated or transmitted by, in the case shown, the ultrasound probe 134 results in optical absorption of the light 114 by the one or more endogenous chromophores 112 (or optical absorbers) and subsequent thermoelastic expansion thereof. Thermoelastic expansion of the one or more endogenous chromophores 112, in turn, generates ultrasound-frequency photoacoustic pressure waves for detection as the ultrasound signals 111 by, in the case shown, the ultrasound transducers 106 of the ultrasound probe 134. Acquisition of ultrasound-signal data by the console 108 allows the ultrasound-signal data to be used to image successive locations in the body of the patient, as shown, track the distal tip of the elongate medical device 110 across successive locations in the body of the patient, or both.

Figure 11:
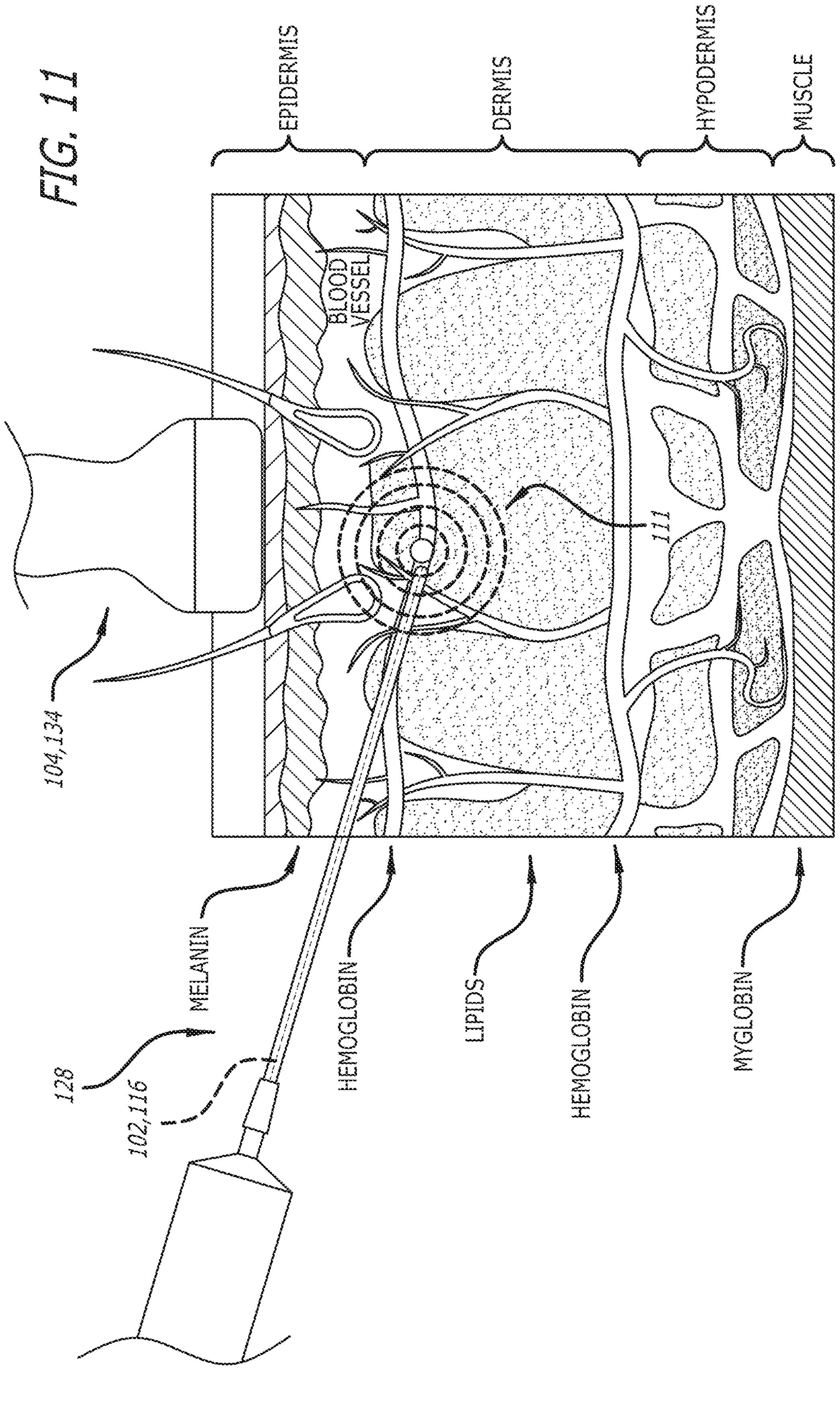
FIG. 11 illustrates detection of the ultrasound signals corresponding to the photoacoustic pressure waves generated from the one or more endogenous chromophores of various tissues using the ultrasound probe in accordance with some embodiments.

FIG. 11 illustrates the one or more endogenous chromophores 112 distributed across different body tissues.

The one or more endogenous chromophores 112 can be selected from at least oxygenated hemoglobin ("$HbO_2$"), reduced hemoglobin ("HbR"), oxygenated myoglobin ("$MbO_2$"), reduced myoglobin ("MbR"), melanin, and one or more lipids, which, endogenous chromophores 112, in turn, can be distributed across different body tissues as shown in FIG. 11. Indeed, melanin and the one or more lipids can be respectively found in skin and adipose tissue, wherein melanin is primarily found in the epidermis and the one or more lipids are primarily found in the hypodermis thereunder. Hemoglobin such as oxygenated hemoglobin and reduced hemoglobin can be found in blood within blood vessels, which blood vessels, in turn, can be found in the dermis, the hypodermis thereunder, and skeletal muscle. Lastly, oxygenated myoglobin and reduced myoglobin can be found in skeletal muscle. Being that the one or more endogenous chromophores 112 can be distributed across different body tissues, such a distribution of the one or more endogenous chromophores 112 can be advantageously utilized by the medical-device navigation system 100 to differentiate such body tissues, for example, when establishing vascular access with the needle 128 as an example of the elongate medical device 110 in accordance with FIG. 11.

Figure 13:
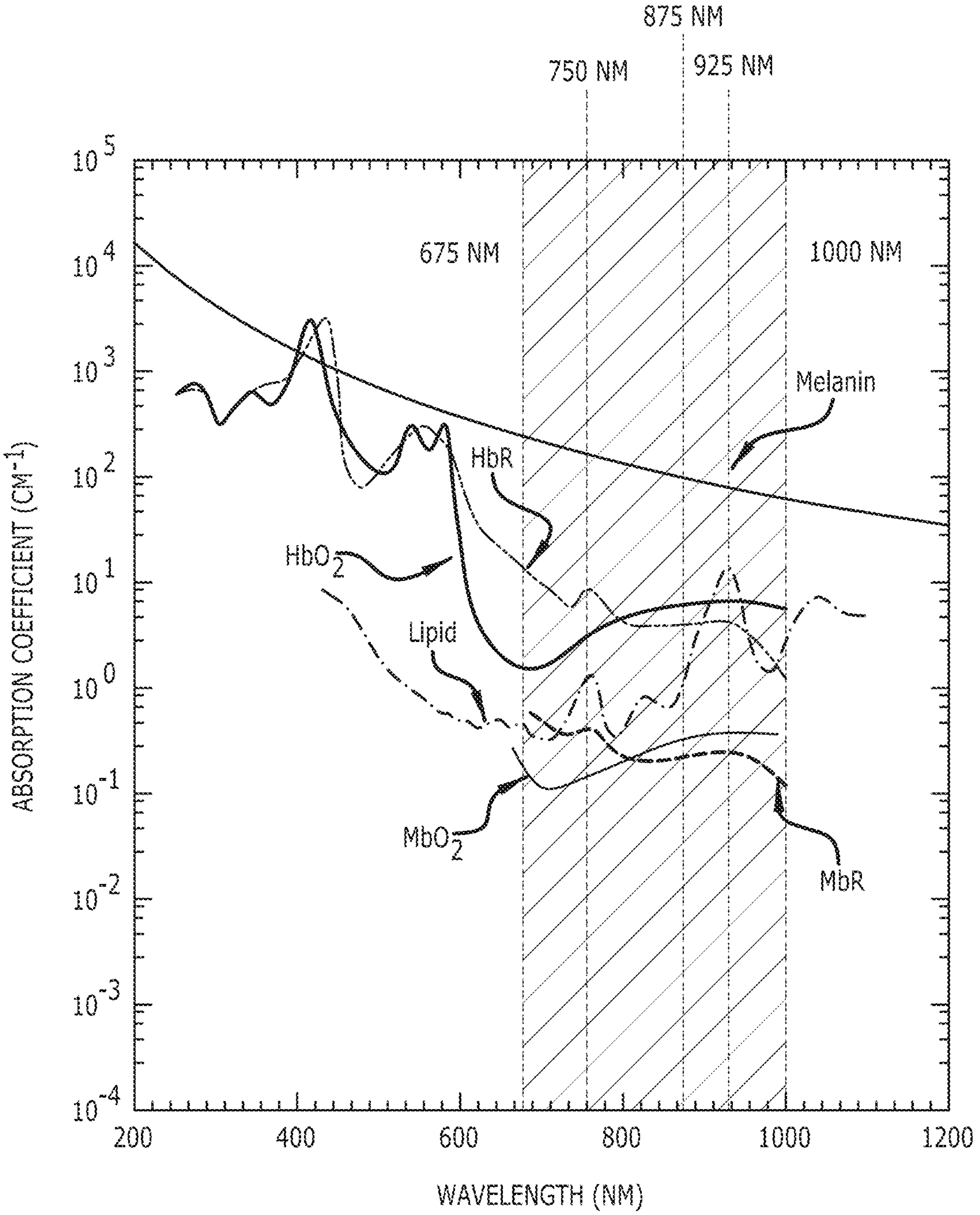
FIG. 13 provides a plot of absorption coefficient vs. wavelength for the one or more endogenous chromophores.

FIG. 13 provides a plot of absorption coefficient vs. wavelength for various endogenous chromophores 112.

As shown by way of the plot of absorption coefficient vs. wavelength for the one or more endogenous chromophores 112, the photoacoustic effect is operative and available to the medical-device navigation system 100 with respect to at least one endogenous chromophore of the one or more endogenous chromophores 112 over an entirety of the wavelength range of light ranging from about 250 nm to about 1100 nm. For example, the photoacoustic effect is operative with respect to both oxygenated hemoglobin and reduced hemoglobin beginning at a wavelength of light about 250 nm, and the photoacoustic effect is operative with respect to the one or more lipids ending at a wavelength of light about 1100 nm. The photoacoustic effect is also operative with respect to each endogenous chromophore of oxygenated hemoglobin, reduced hemoglobin, oxygenated myoglobin, reduced myoglobin, melanin, and one or more lipids over an entirety of the wavelength range of light ranging from about 675 nm to about 1000 nm, which, notably, falls within the so-called therapeutic window of light, wherein light has its greatest depth of penetration in biological tissue.

Oxygenated hemoglobin, reduced hemoglobin, oxygenated myoglobin, reduced myoglobin, melanin, and one or more lipids are also distinguishable from each other over the 675-1000-nm wavelength range of light in view of their different absorption coefficients. Indeed, the absorption coefficients for the foregoing endogenous chromophores 112 are sufficiently spread apart from each other over about three orders of magnitude in the 675-1000-nm wavelength range of light for distinguishing them from each other. For example, the absorption coefficients for oxygenated hemoglobin, reduced hemoglobin, oxygenated myoglobin, reduced myoglobin, melanin, and the one or more lipids are sufficiently spread apart from each other at each wavelength selected from the approximate wavelengths of 750 nm, 875 nm, and 925 nm for distinguishing them from each other. As such, the medical-device navigation system 100 can utilize the photoacoustic effect in the foregoing wavelength ranges or at the foregoing wavelengths thereof to differentiate body tissues, as above, when establishing vascular access with the needle 128 as shown in FIG. 11. Indeed, at a wavelength of about 750 nm, for example, absorption coefficients for melanin, reduced hemoglobin, oxygenated hemoglobin, the one or more lipids, reduced myoglobin, and oxygenated myoglobin vary over about three orders of magnitude from greatest to least in the foregoing order, thereby leading to a reduction in ultrasound-signal intensity and image contrast in any reconstructed images as the foregoing needle 128 successively passes through the epidermis, one or more blood vessels in the dermis or hypodermis, adipose tissue such as that of the hypodermis, and, finally, skeletal muscle. Differentiation of such body tissues can be advantageously extracted during the signal-processing process and indicated via labels on ultrasound images, thereby allowing clinicians to confirm, in real-time, different body tissues as they are visualized in the ultrasound images while establishing vascular access.

Adverting back to FIGS. 1 and 2, the stylet 102 can be configured to removably insert into a lumen of the elongate medical device 110, as shown, or the stylet 102 can be integrated into the elongate medical device 110, thereby making the elongate medical device 110, itself, part of the medical-device navigation system 100. Regardless, such a stylet 102 includes an optical fiber 116 along a length of the stylet 102 configured to transmit the light 114 from the light source 144 of the console 108 to a distal tip of the elongate medical device 110. When the elongate medical device 110 is disposed in a body of a patient, the light 114 transmitted from the light source 144 irradiates the one or more endogenous chromophores 112 in an instant location of the distal tip of the elongate medical device 110 to generate ultrasound-frequency photoacoustic pressure waves therefrom, which photoacoustic pressure waves can be detected as the ultrasound signals 111.

As shown in at least FIG. 1, the elongate medical device 110 can be a catheter 118 including a catheter tube 120, a furcated hub 122 (e.g., a bifurcated hub, a trifurcated hub, etc.), a plurality of extension legs 124 (e.g., two extension legs, three extension legs, etc.), and a plurality of fluid fittings 126 (e.g., two Luer connectors, three Luer connectors, etc.) operably connected in the foregoing order for a multiluminal catheter such as the peripherally inserted central catheter ("PICC") shown. Notwithstanding the foregoing, it should be understood that the catheter 118 can alternatively be a monoluminal catheter in some embodiments. Regardless, the catheter 118 can include at least one lumen into which the stylet 102 is configured to be removably inserted should the stylet 102 not be integrated into the catheter 118. In embodiments in which the stylet 102 is integrated into the catheter 118, it is integrated into a longitudinal bead of the catheter 118 tube such as along a septum or catheter-tube wall of the catheter tube 120 and, further, along a hub channel of the furcated hub 122. Such a catheter 118 can further include an extension tube akin to an extension leg 124 extending from the furcated hub 122, albeit with the stylet 102 disposed therein. Such an extension tube can terminate in a plug like that illustrated for the stylet 102 of FIG. 1 for establishing an optical connection between the catheter 118 and the light source 144 of the console 108.

Figure 9:
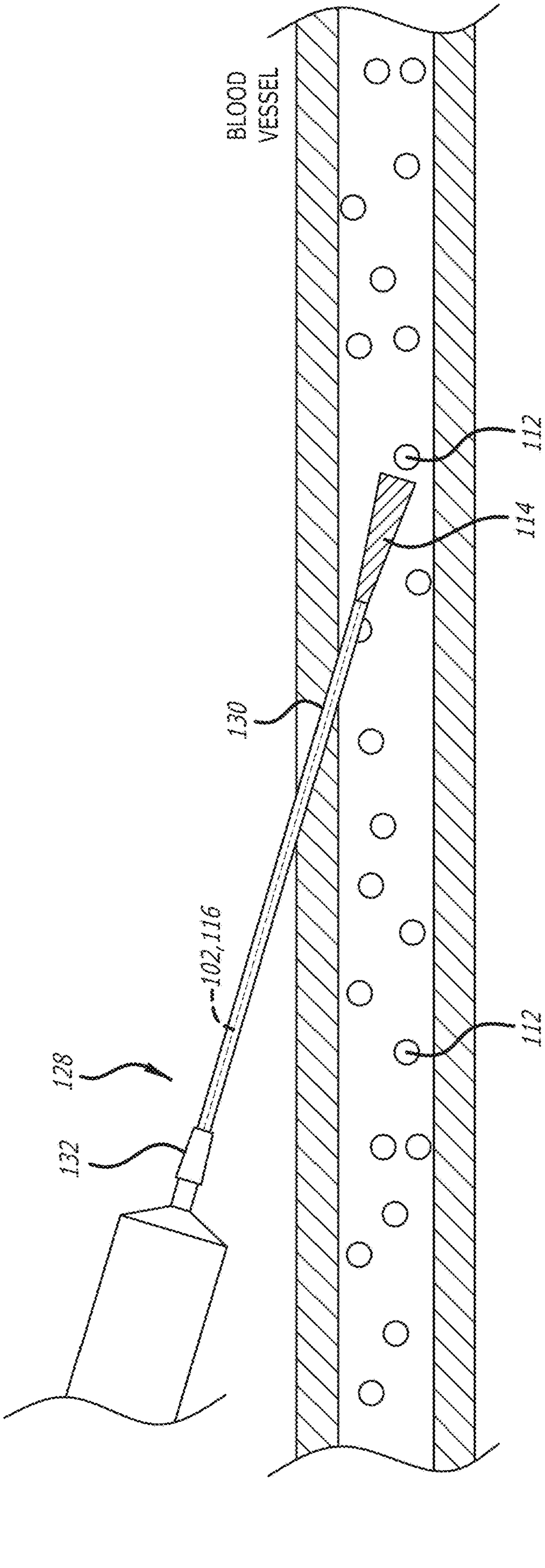
FIG. 9 illustrates irradiation of the one or more endogenous chromophores from a distal tip of a needle in accordance with some embodiments.
Figure 10:
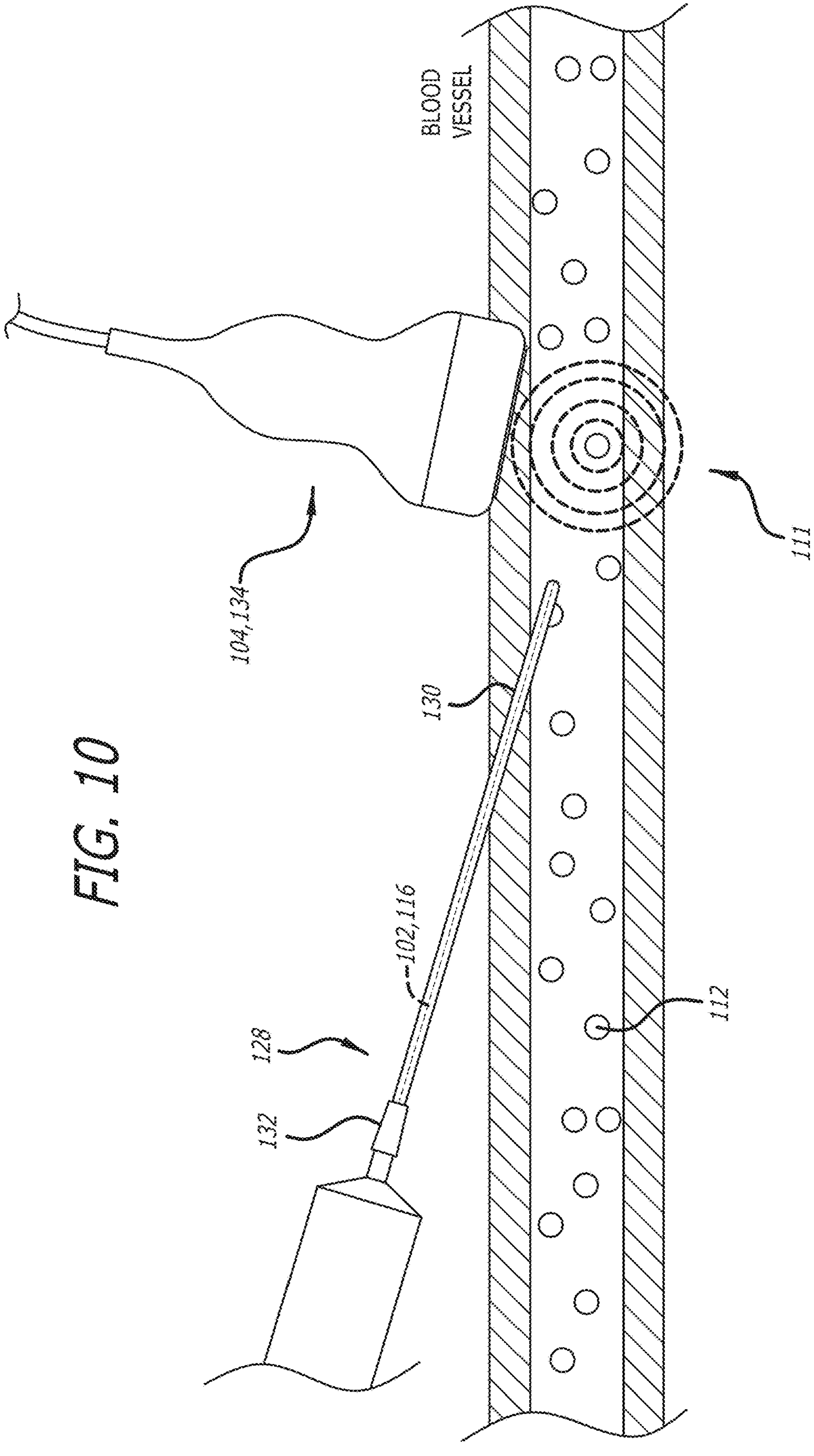
FIG. 10 illustrates detection of the ultrasound signals corresponding to the photoacoustic pressure waves generated from the one or more endogenous chromophores using the ultrasound probe in accordance with some embodiments.

As shown in FIGS. 9-11, the elongate medical device 110 can be a needle 128 including a needle shaft 130 and a needle hub 132 over a proximal end portion of the needle shaft 130. The needle 128 can include a lumen into which the stylet 102 is configured to be removably inserted should the stylet 102 not be integrated into the needle 128. In embodiments in which the stylet 102 is integrated into the needle 128, it is integrated into a longitudinal channel of the needle shaft 130 and, further, along a hub channel of the needle hub 132. Such a needle 128 can further include an extension tube extending from the needle 128 hub with the stylet 102 disposed therein. Such an extension tube can terminate in a plug like that illustrated for the stylet 102 of FIG. 1 for establishing an optical connection between the needle 128 and the light source 144 of the console 108.

Figure 5:
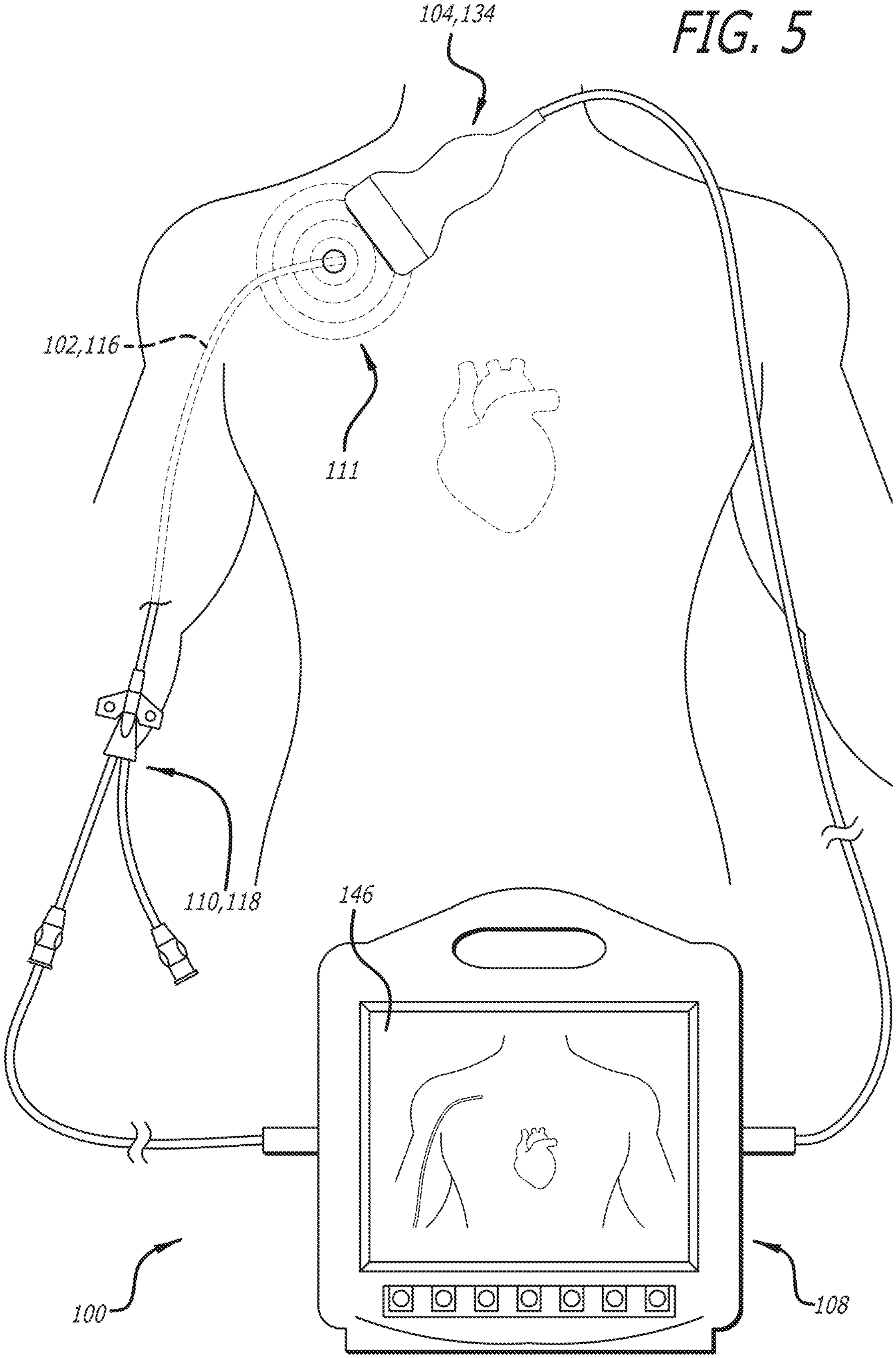
FIG. 5 illustrates navigation of the catheter in a body of a patient with the medical-device navigation system and the ultrasound probe thereof in accordance with some embodiments.
Figure 6:
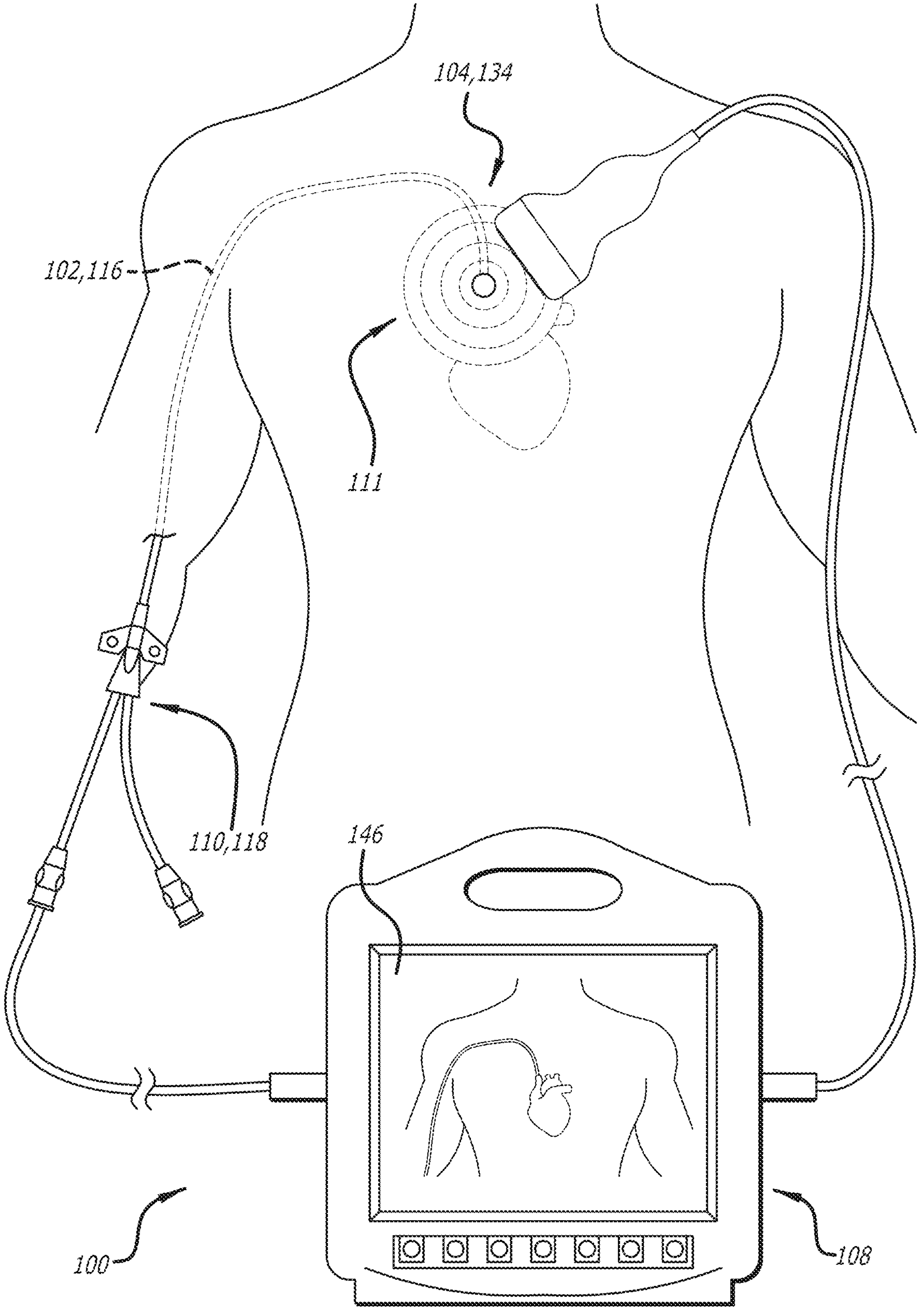
FIG. 6 illustrates placement of the distal tip of the catheter in a superior vena cava ("SVC) of the patient with the medical-device navigation system and the ultrasound probe thereof in accordance with some embodiments.

The ultrasound transducers 106 can be disposed in a sensor array of an ultrasound probe 134 as the ultrasound device 104 shown in FIGS. 1, 5, and 6, which ultrasound probe 134 can notably double as an ultrasound-imaging ultrasound probe in addition to its function of detecting the ultrasound signals 111 corresponding to the photoacoustic pressure waves. Alternatively, the ultrasound transducers 106 can be disposed in a plurality of patient-wearable patches 136 as the ultrasound devices 104 shown in FIGS. 7 and 8, which patient-wearable patches 136 can also notably be accompanied by an ultrasound-imaging ultrasound probe in accordance with some embodiments. Regardless, the ultrasound transducers 106 in the sensor array of the ultrasound probe 134 and the patient-wearable patches 136 are configured to detect the ultrasound signals 111 propagated through one or more tissues of a patient corresponding to the photoacoustic pressure waves generated from the one or more endogenous chromophores 112. Without limitation, the ultrasound transducers 106 in the sensor array of the ultrasound probe 134 or those of the patient-wearable patches 136 can be piezoelectric transducers or capacitive micromachined ultrasonic transducers ("CMUTs").

The console 108 includes electronic components and circuitry including computer-readable memory 138, one or more processors 140, logic 142, a light source 144 such as a laser, and a display 146. The memory 138 can include primary memory such as RAM, cache memory, ROM, or the like and, optionally, secondary memory such as that of a secondary storage device. The primary, read-only memory includes at least a portion of a set of executable instructions 148 configured to instantiate medical-device navigation processes of the console 108 upon execution by the processor(s) 140 for navigating the elongate medical device 110 by way of the stylet 102 disposed therein as the elongate medical device 110 is advanced to a target location in a body of a patient. The light source 144 can be integrated into the console 108, or the light source 144 can be integrated into another component of the medical-device navigation system 100 such as a stand-alone light-source module configured to operably connect to the console 108. The display 146 can be integrated into the console 108, or the display 146 can be integrated into another component of the medical-device navigation system 100 such as a stand-alone monitor configured to operably connect to the console 108. Notably, the console 108 can assume any convenient form factor including that of a smart device such as a smartphone or tablet, and, in such embodiments, at least the light source 144 can be the stand-alone light-source module.

Figure 8:
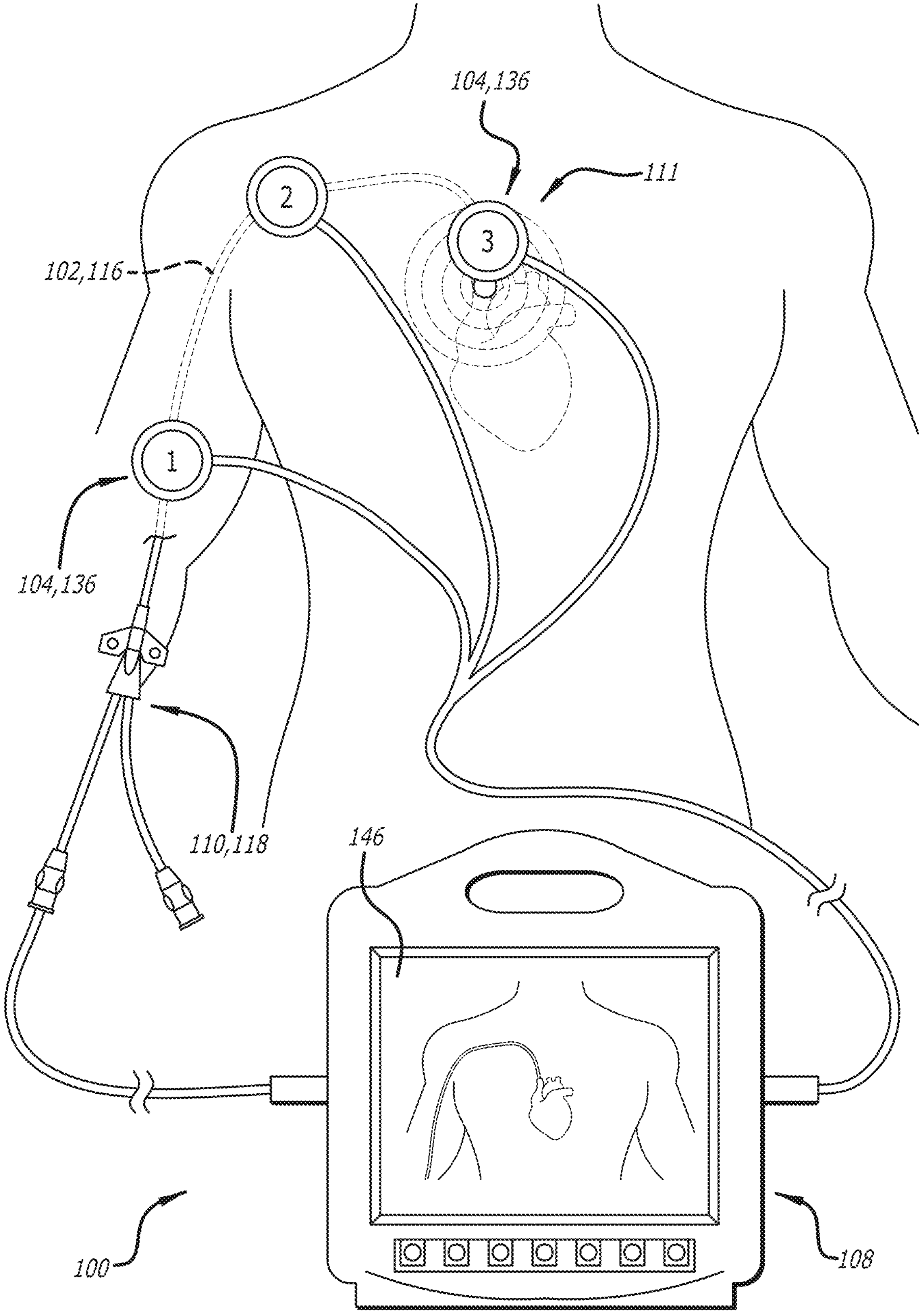
FIG. 8 illustrates placement of the distal tip of the catheter in the SVC of the patient with the medical-device navigation system and the plurality of patient-wearable ultrasound-transducer patches thereof in accordance with some embodiments.

As set forth above, the medical-device navigation system 100 utilizes the photoacoustic effect to generate the ultrasound signals 111 at an instant location of the distal tip of the elongate medical device 110 in the body of the patient, which ultrasound signals 111 can be detected and acquired for up to at least three navigation modalities. In a first navigation modality, the medical-device navigation system 100 utilizes the photoacoustic effect for imaging successive locations in the body of the patient. Successively imaged locations in the body of the patient can be composited into a composite image or representation thereof on the display 146 as shown in FIGS. 5 and 6, thereby providing a tracking path for the elongate medical device 110. In a second navigation modality, the medical-device navigation system 100 also utilizes the photoacoustic effect but not necessarily for imaging successive locations in the body of the patient. Indeed, the medical-device navigation system 100 can utilize the photoacoustic effect to alternatively or additionally differentiate among body tissues, for example, on ultrasound images, akin to that shown in FIG. 11. In a third navigation modality, the medical-device navigation system 100 utilizes the photoacoustic effect for tracking the distal tip of the elongate medical device 110 by its ultrasound signals 111 across the successive locations in the body of the patient. Successive locations of the distal tip of the elongate medical device 110 in the body of the patient can be concatenated on the display 146 as shown in FIGS. 7 and 8, thereby providing a tracking path for the elongate medical device 110. However, it should be understood that the medical-device navigation system 100 is not limited to a single navigation modality or structural configuration described therefor. Indeed, the structural configuration of the medical-device navigation system 100 can vary, as needed, to provide any one or more navigation modalities set forth herein, optionally, in combination with those disclosed in U.S. Pat. Nos. 8,388,541; 8,781,555; 8,849,382; 9,636,031; and 9,649,048, each of which is incorporated by reference in its entirety into this application.

As to the first navigation modality, the medical-device navigation processes can include one or more processes selected from at least an irradiation process, a data-acquisition process, a signal-processing process, a mapping process, an image-reconstruction process, a compositing process, and a displaying process.

Figure 3:
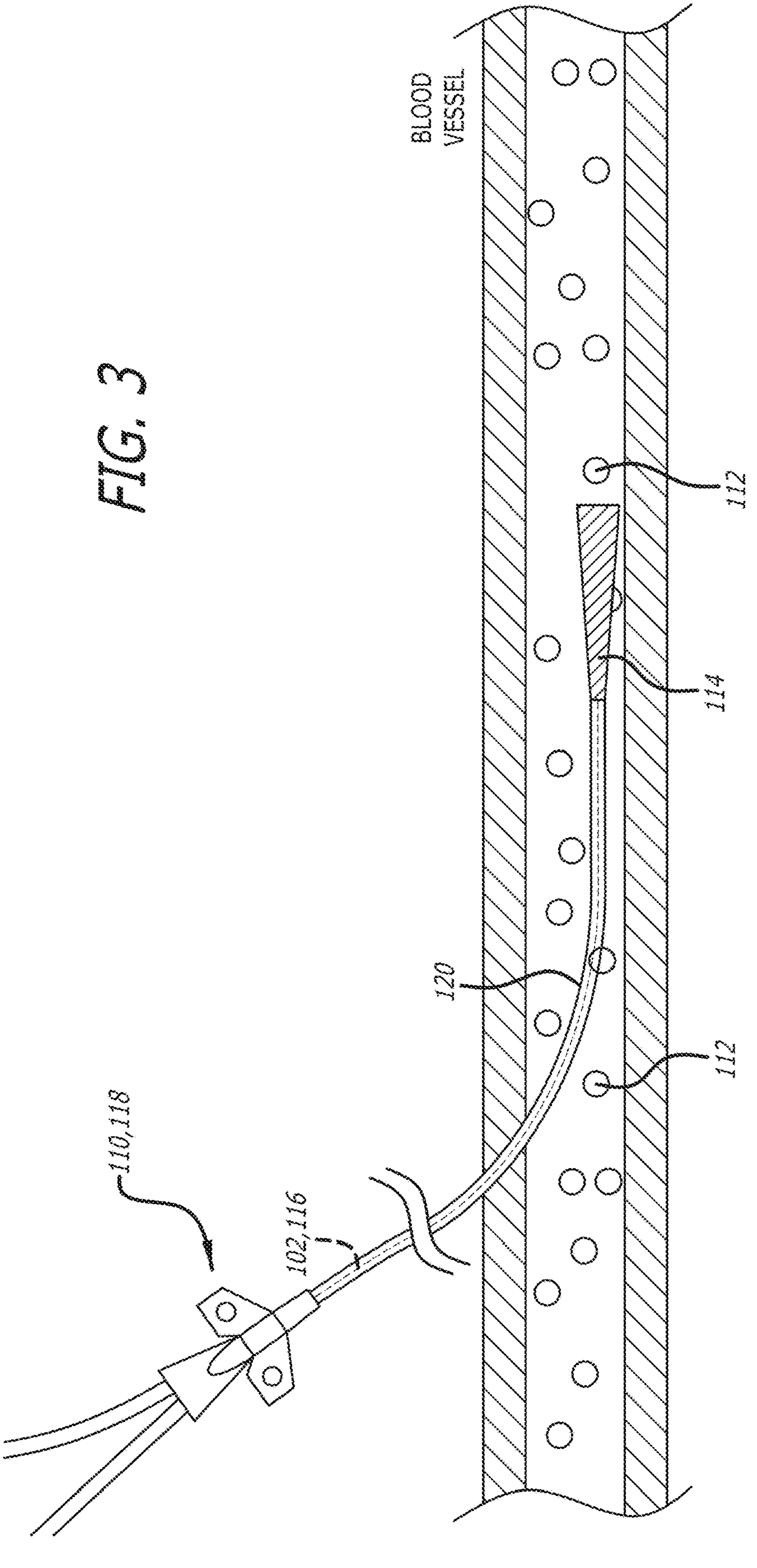
FIG. 3 illustrates irradiation of one or more endogenous chromophores from a distal tip of a catheter in accordance with some embodiments.
Figure 4:
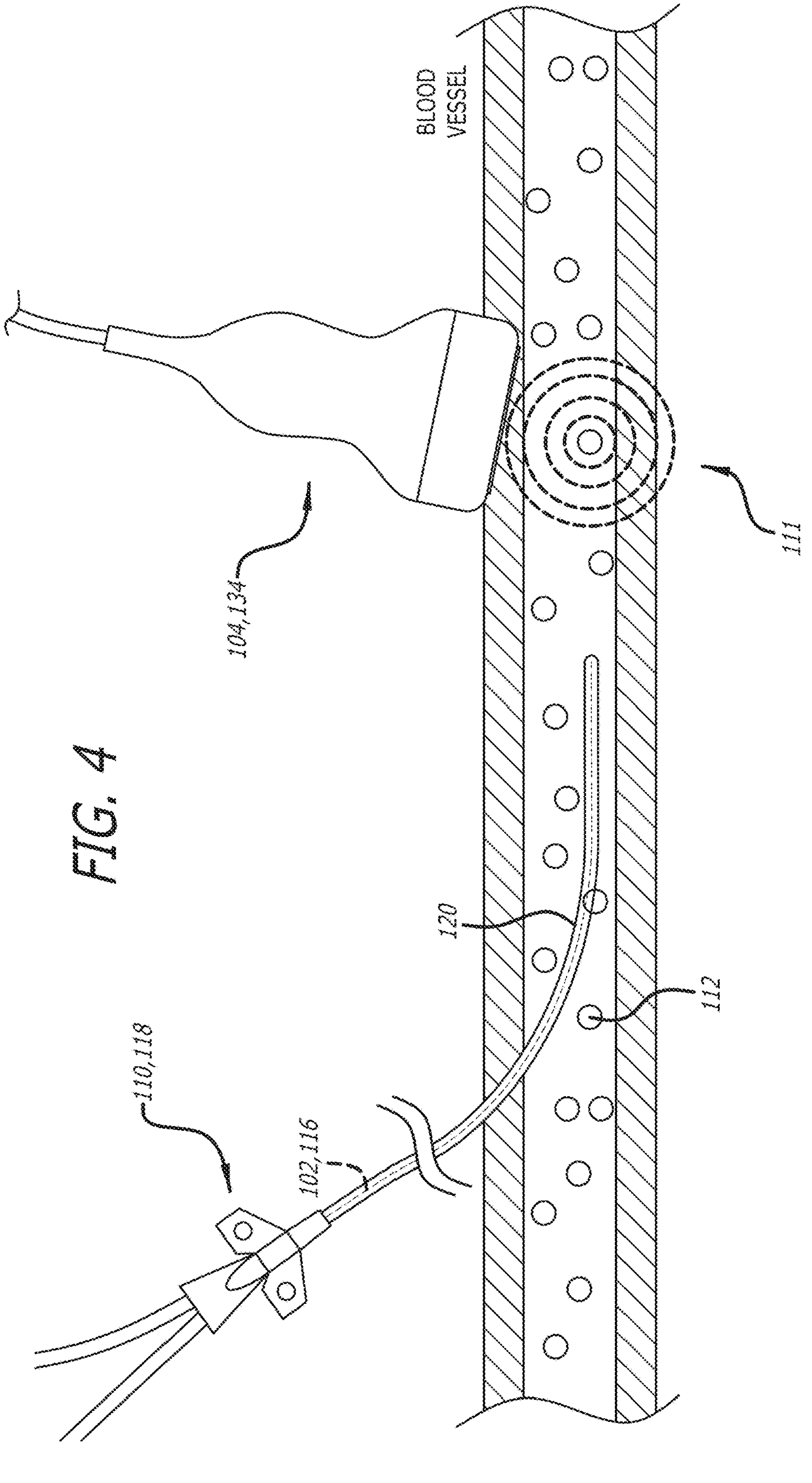
FIG. 4 illustrates detection of ultrasound signals corresponding to photoacoustic pressure waves generated from the one or more endogenous chromophores using an ultrasound probe in accordance with some embodiments.

FIG. 3 illustrates irradiation of the one or more endogenous chromophores 112 from a distal tip of the catheter 118 in accordance with some embodiments. FIG. 9 illustrates irradiation of the one or more endogenous chromophores 112 from a distal tip of the needle 128 in accordance with some embodiments.

Whether the elongate medical device 110 is the catheter 118 or the needle 128 set forth above, the irradiation process can utilize irradiation logic for irradiating the one or more endogenous chromophores 112 in the instant location of the distal tip of the elongate medical device 110 in the body of the patient with the light 114 provided by the light source 144 and transmitted by the optical fiber 116. The light 114 provided by the light source 144 can be a pulsed light or intensity-modulated continuous light for optical absorption and thermoelastic expansion of the one or more endogenous chromophores 112. Notably, the optical absorption and thermoelastic expansion of the one or more endogenous chromophores 112 and, thus, the photoacoustic pressure waves and the corresponding ultrasound signals 111 vary in accordance with the pulsed light or the intensity-modulated continuous light.

Notably, FIG. 12 illustrates irradiation of the one or more endogenous chromophores 112 with the ultrasound probe 134 in accordance with some embodiments. It should be understood that while the medical-device navigation system 100 is primarily described with respect to irradiating the one or more endogenous chromophores 112 in the instant location of the distal tip of the elongate medical device 110, this does not preclude irradiating the one or more endogenous chromophores 112 with the ultrasound probe 134 in accordance with some embodiments.

FIGS. 4-8, 10, and 11 illustrates detection of the ultrasound signals 111 corresponding to the photoacoustic pressure waves generated from the one or more endogenous chromophores 112 using the ultrasound probe 134 or the patient-wearable patches 136 in accordance with some embodiments.

The data-acquisition process can utilize data-acquisition logic for acquiring ultrasound-signal data from the ultrasound transducers 106 of the ultrasound probe 134 or the patient-wearable patches 136 and writing the ultrasound-signal data to the memory 138 of the console 108.

The signal-processing process can utilize signal-processing logic for at least extracting time-of-flight information from the ultrasound-signal data and writing the time-of-flight information to the memory 138 of the console 108. Extracting such time-of-flight information from the ultrasound-signal data can include determining time delays between pulses or modulations of the light 114 and arrivals of the corresponding ultrasound signals 111 at one or more ultrasound transducers 106.

The mapping process can utilize mapping logic for mapping the ultrasound signals 111 from different ultrasound transducers 106 to common photoacoustic pressure-wave sources or events using the time-of-flight information and speed of sound in the instant location of the distal tip of the elongate medical device 110 in the body of the patient.

The image-reconstruction process can utilize image-reconstruction logic for reconstructing images from the ultrasound-signal data and writing image data to the memory 138 of the console 108. Indeed, the image-reconstruction process can reconstruct the images for navigating the elongate medical device 110 by projecting mapped ultrasound signals from the mapping process back along their possible paths from the different ultrasound transducers 106 to the common photoacoustic pressure-wave sources or events.

The compositing process can utilize compositing logic for compositing successively imaged locations in the body of the patient into a composite image for the display 146, thereby providing a tracking path for the elongate medical device 110.

The displaying process can utilize displaying logic for displaying reconstructed images, composite images, or any tracking path provided thereby from the image data on the display 146, optionally, over a patient avatar, as shown, for navigating the elongate medical device 110 to the target location in the body of the patient.

As to the second navigation modality, the medical-device navigation processes can include one or more processes selected from at least the foregoing irradiation process, the foregoing data-acquisition process, a signal-processing process, a labeling process, and a displaying process.

Following on from the data-acquisition process from the first navigation modality, the signal-processing process can utilize signal-processing logic for at least extracting ultrasound-signal intensities from the ultrasound-signal data and writing the ultrasound-signal intensities to the memory 138 of the console 108. Being as such ultrasound-signal intensities reduce in magnitude from the epidermis, one or more blood vessels in the dermis or hypodermis, adipose tissue such as that of the hypodermis, and, finally, skeletal muscle, such ultrasound-signal intensities can be used to indicate a body tissue in which the distal tip of the elongate medical device 110 is disposed.

The labeling process can utilize labeling logic for labeling ultrasound images to indicate different body tissues, thereby allowing clinicians to confirm, in real-time, the different body tissues as they are visualized in the ultrasound images.

The displaying process can utilize displaying logic for displaying the ultrasound images with the labels for the different body tissues for navigating the elongate medical device 110 to the target location in the body of the patient.

As to the third navigation modality, the medical-device navigation processes can include one or more processes selected from at least the foregoing irradiation process, the foregoing data-acquisition process, a signal-processing process, a mapping process, and a displaying process.

Following on from the data-acquisition process from the first navigation modality, the signal-processing process can, like that of the second navigation modality, utilize the signal-processing logic for at least extracting ultrasound-signal intensities from the ultrasound-signal data and writing the ultrasound-signal intensities to the memory 138 of the console 108. However, different than the second navigation modality, the ultrasound-signal intensities that vary in accordance with distances from the ultrasound transducers 106 of the ultrasound probe 134 or the patient-wearable patches 136 are written to the memory 138 of the console 108.

Like that of the first navigation modality, the mapping process can utilize the mapping logic for mapping the ultrasound signals 111 from different ultrasound transducers 106 to common photoacoustic pressure-wave sources or events in successive locations of the distal tip of the elongate medical device 110 in the body of the patient. Successive locations of the distal tip of the elongate medical device 110 in the body of the patient can be concatenated on the display 146 as shown in FIGS. 7 and 8, thereby providing a tracking path for the elongate medical device 110.

The displaying process can utilize displaying logic for displaying the tracking path for the elongate medical device 110 for navigating the elongate medical device 110 to the target location in the body of the patient.

While some particular embodiments have been disclosed herein, and while the particular embodiments have been disclosed in some detail, it is not the intention for the particular embodiments to limit the scope of the concepts provided herein. Additional adaptations or modifications can appear to those of ordinary skill in the art, and, in broader aspects, these adaptations or modifications are encompassed as well. Accordingly, departures may be made from the particular embodiments disclosed herein without departing from the scope of the concepts provided herein.

What is claimed is:

1. A medical-device navigation system for navigating an elongate medical device to a target location in a body of a patient, the medical-device navigation system comprising:

- a stylet including an optical fiber along a length of the stylet, the optical fiber configured to transmit light to an instant location of a distal tip of the elongate medical device in the body of the patient for irradiating one or more endogenous chromophores in the instant location to generate ultrasound-frequency photoacoustic pressure waves therefrom;
- a plurality of ultrasound transducers disposed in a plurality of patient-wearable patches for locating the elongate medical device within a patient-based reference frame while navigating the elongate medical device to the target location in the body of the patient, the plurality of ultrasound transducers configured to detect ultrasound signals propagated through one or more tissues of the patient, and the ultrasound signals corresponding to the ultrasound-frequency photoacoustic pressure waves generated from the one or more endogenous chromophores; and
- a console with electronic components and circuitry including memory and one or more processors, the memory including executable instructions configured to instantiate medical-device navigation processes upon execution by the one or more processor(s) for navigating the elongate medical device by way of the stylet disposed therein as the elongate medical device is advanced to the target location in the body of the patient, and the medical-device navigation processes including:
  - a data-acquisition process that utilizes data-acquisition logic for acquiring ultrasound-signal data from the plurality of ultrasound transducers and writing the ultrasound-signal data to the memory of the console;
  - an image-reconstruction process that utilizes image-reconstruction logic for reconstructing images from the ultrasound-signal data and writing image data to the memory of the console; and
  - a displaying process that utilizes displaying logic for displaying reconstructed images from the image data on a display for navigating the elongate medical device to the target location in the body of the patient.

2. The medical-device navigation system of claim 1, the medical-device navigation processes further including an irradiation process that utilizes irradiation logic for irradiating the one or more endogenous chromophores in the instant location with the light transmitted by the optical fiber, the light being a pulsed light or an intensity-modulated continuous light for optical absorption and thermoelastic expansion of the one or more endogenous chromophores.

3. The medical-device navigation system of claim 2, wherein the optical absorption and thermoelastic expansion of the one or more endogenous chromophores and, thus, the ultrasound-frequency photoacoustic pressure waves and the corresponding ultrasound signals vary in accordance with the pulsed light or the intensity-modulated continuous light.

4. The medical-device navigation system of claim 1, the medical-device navigation processes further including a signal-processing process that utilizes signal-processing logic for at least extracting time-of-flight information from the ultrasound-signal data.

5. The medical-device navigation system of claim 4, the medical-device navigation processes further including a mapping process that utilizes mapping logic for mapping the ultrasound signals from different patient-wearable patches to common photoacoustic pressure-wave sources or events with the time-of-flight information and speed of sound in the instant location of the distal tip of the elongate medical device in the body of the patient.

6. The medical-device navigation system of claim 5, wherein the image-reconstruction process reconstructs the images for navigating the elongate medical device by projecting mapped ultrasound signals from the mapping process back along their possible paths from different ultrasound transducers to the common photoacoustic pressure-wave sources or events.

7. The medical-device navigation system of claim 5, wherein the one or more endogenous chromophores are selected from at least oxygenated hemoglobin, reduced hemoglobin, oxygenated myoglobin, reduced myoglobin, melanin, melanin, and one or more lipids.

8. The medical-device navigation system of claim 1, wherein the stylet is configured to removably insert into a lumen of the elongate medical device.

9. The medical-device navigation system of claim 1, wherein the stylet is integrated into the elongate medical device.

10. A method of a medical-device navigation system for navigating an elongate medical device to a target location in a body of a patient, the method comprising:

instantiating medical-device navigation processes upon executing executable instructions stored in memory of a console by one or more processors of the console, the medical-device navigation processes for navigating the elongate medical device by way of an optical-fiber stylet disposed therein as the elongate medical device is advanced to the target location in the body of the patient;

transmitting light along a length of the stylet to an instant location of a distal tip of the elongate medical device in the body of the patient and irradiating one or more endogenous chromophores in the instant location to generate ultrasound-frequency photoacoustic pressure waves therefrom;

detecting ultrasound signals with a plurality of ultrasound transducers disposed in a plurality of patient-wearable patches for locating the elongate medical device within a patient-based reference frame while navigating the elongate medical device to the target location in the body of the patient, the ultrasound signals propagated through one or more tissues of the patient, and the ultrasound signals corresponding to the ultrasound-frequency photoacoustic pressure waves generated from the one or more endogenous chromophores;

acquiring ultrasound-signal data from the plurality of ultrasound transducers and writing the ultrasound-signal data to the memory of the console in accordance with a data-acquisition process that utilizes data-acquisition logic;

reconstructing images from the ultrasound-signal data and writing image data to the memory of the console in accordance with an image-reconstruction process that utilizes image-reconstruction logic; and displaying reconstructed images from the image data on a display in accordance with a displaying process that utilizes displaying logic for navigating the elongate medical device to the target location in the body of the patient.

11. The method of claim 10, further comprising irradiating the one or more endogenous chromophores in the instant location with the light transmitted by an optical fiber, the light being a pulsed light or intensity-modulated continuous light in accordance with an irradiation process that utilizes irradiation logic for optical absorption and thermoelastic expansion of the one or more endogenous chromophores.

12. The method of claim 11, wherein the thermoelastic expansion of the one or more endogenous chromophores and, thus, the ultrasound-frequency photoacoustic pressure waves and the corresponding ultrasound signals vary in accordance with the pulsed light or the intensity-modulated continuous light.

13. The method of claim 10, further comprising extracting time-of-flight information from the ultrasound-signal data in accordance with a signal-processing process that utilizes signal-processing logic.

14. The method of claim 13, further comprising mapping the ultrasound signals from different ultrasound transducers to common photoacoustic pressure-wave sources or events with the time-of-flight information and speed of sound in the instant location of the distal tip of the elongate medical device in the body of the patient in accordance with a mapping process that utilizes mapping logic.

15. The method of claim 14, wherein the image-reconstruction process reconstructs the images for navigating the elongate medical device by projecting mapped ultrasound signals from the mapping process back along their possible paths from the different ultrasound transducers to the common photoacoustic pressure-wave sources or events.

16. The method of claim 14, wherein the one or more endogenous chromophores are selected from at least oxygenated hemoglobin, reduced hemoglobin, oxygenated myoglobin, reduced myoglobin, melanin, and one or more lipids.

17. The method of claim 10, wherein the optical-fiber stylet is configured to removably insert into a lumen of the elongate medical device.

18. The method of claim 10, wherein the optical-fiber stylet is integrated into the elongate medical device.

19. A medical-device navigation system for navigating an elongate medical device to a target location in a body of a patient, the medical-device navigation system comprising:

a stylet including an optical fiber along a length of the stylet, the optical fiber configured to transmit light to an instant location of a distal tip of the elongate medical device in the body of the patient for irradiating one or more endogenous chromophores in the instant location to generate ultrasound-frequency photoacoustic pressure waves therefrom;

a plurality of ultrasound transducers disposed in a plurality of patient-wearable patches for locating the elongate medical device within a patient-based reference frame while navigating the elongate medical device to the target location in the body of the patient, the plurality of ultrasound transducers configured to detect ultrasound signals corresponding to the ultrasound-frequency photoacoustic pressure waves generated from the one or more endogenous chromophores; and a console with electronic components and circuitry including memory and one or more processors, the memory including executable instructions configured to instantiate medical-device navigation processes upon execution by the one or more processor(s) for navigating the elongate medical device by way of the stylet disposed therein as the elongate medical device is advanced to the target location in the body of the patient, and the medical-device navigation processes including:

a data-acquisition process that utilizes data-acquisition logic for acquiring ultrasound-signal data from the plurality of ultrasound transducers and writing the ultrasound-signal data to the memory of the console;

a mapping process that utilizes mapping logic for mapping the ultrasound signals from different patient-wearable patches to common photoacoustic pressure-wave sources or events with time-of-flight information and speed of sound in the instant location of the distal tip of the elongate medical device in the body of the patient;

an image-reconstruction process that utilizes image-reconstruction logic for reconstructing images from the ultrasound-signal data and writing image data to the memory of the console; and a displaying process that utilizes displaying logic for displaying reconstructed images from the image data on a display for navigating the elongate medical device to the target location in the body of the patient.

20. The medical-device navigation system of claim 19, the medical-device navigation processes further including a signal-processing process that utilizes signal-processing logic for at least extracting the time-of-flight information from the ultrasound-signal data.

21. The medical-device navigation system of claim 19, wherein the image-reconstruction process reconstructs the images for navigating the elongate medical device by projecting mapped ultrasound signals from the mapping process back along their possible paths from the different patient-wearable patches to the common photoacoustic pressure-wave sources or events.

22. The medical-device navigation system of claim 19, the displaying process further including displaying the reconstructed images on the display over a patient avatar for navigating the elongate medical device to the target location in the body of the patient.

23. The medical-device navigation system of claim 19, wherein the elongate medical device is a catheter and the stylet is integrated into the catheter or configured to be removably inserted into a lumen of the catheter.

* * * * *